United States Patent [19]
Easter

[11] Patent Number: 6,048,502
[45] Date of Patent: *Apr. 11, 2000

[54] WATER RECIRCULATING STERILIZATION MECHANISM

[76] Inventor: Basil O. Easter, P.O. Box 328, Milan, Ill. 61264

[ * ] Notice: This patent issued on a continued prosecution application filed under 37 CFR 1.53(d), and is subject to the twenty year patent term provisions of 35 U.S.C. 154(a)(2).

[21] Appl. No.: 08/622,387

[22] Filed: Mar. 27, 1996

[51] Int. Cl.⁷ ........................................................ A61L 2/06
[52] U.S. Cl. ............................................ 422/298; 422/307
[58] Field of Search ............................ 422/26, 295, 298, 422/307

[56] References Cited

U.S. PATENT DOCUMENTS 4,808,377   2/1989   Childers et al. ........................... 422/26

Primary Examiner—Ivars Cintins
Attorney, Agent, or Firm—Rockey, Milnamow & Katz, Ltd.

[57] ABSTRACT

A sterilization mechanism which includes a first conduit extending between a water tank and a sterilization chamber. A heat source operatively coupled with the first conduit converts water from the water tank into steam for sterilizing objects within the chamber. A second conduit extends from the chamber to the tank for recirculating fluids from the chamber back to the water tank.

2 Claims, 1 Drawing Sheet

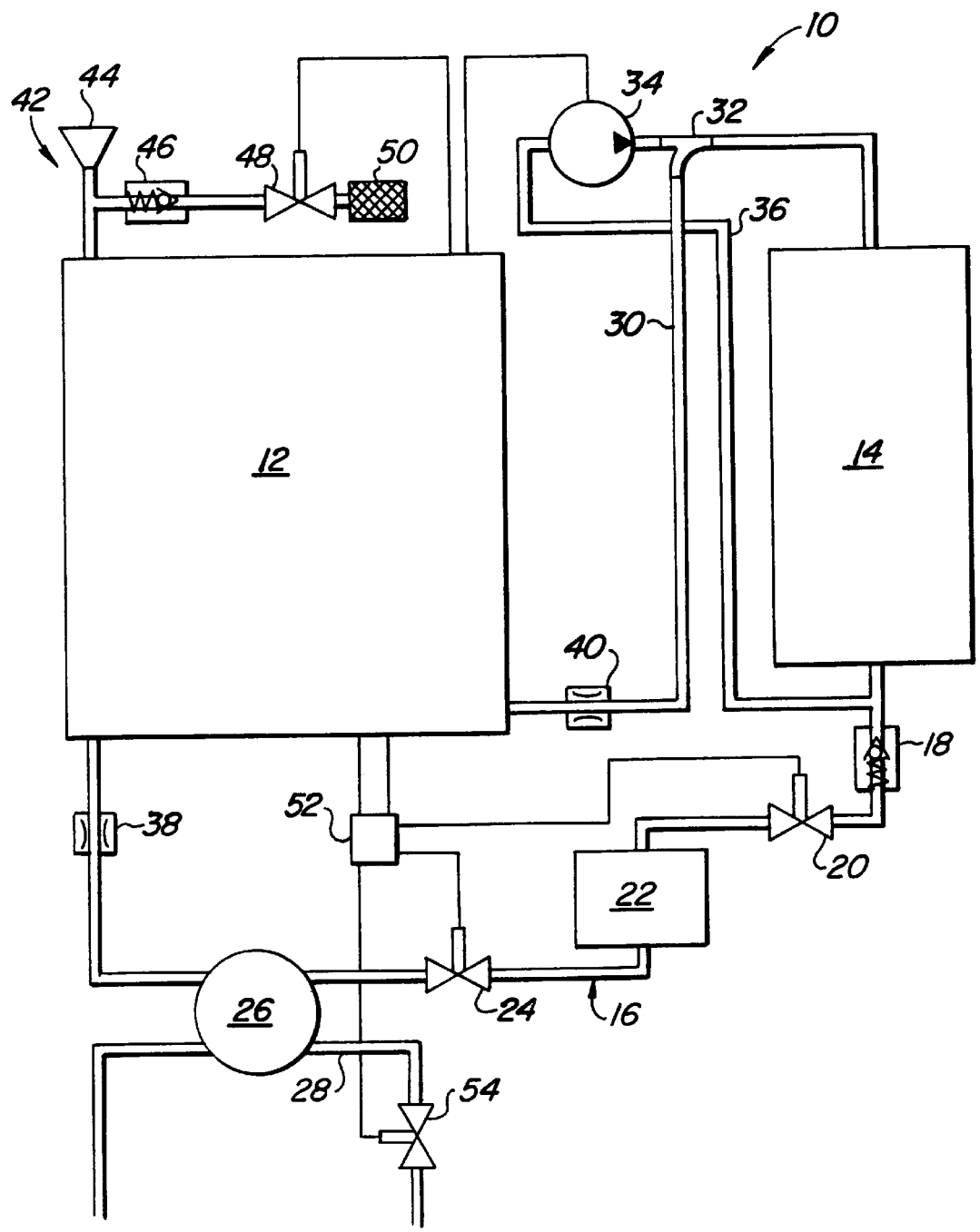

8,048,502

WATER RECIRCULATING STERILIZATION MECHANISM

BACKGROUND OF THE INVENTION

1) Field of the Invention

This invention relates to autoclaves or sterilization mechanisms which utilize steam and extreme heat to sterilizing objects.

2) Related Art

Conventional autoclaves, otherwise known as sterilizers, operate to sterilize objects such as surgical instruments by introducing steam at a relatively high temperature into a sterilization chamber. The high temperature steam within the chamber serves to kill any bacteria or germs which are present on the objects within the chamber.

Conventional sterilizers are also often provided with vacuum mechanisms which serve to create suction to draw the steam and other gasses and fluids from the chamber. These vacuum mechanisms serve to condition the objects both before the sterilization process begins and after the sterilization process is completed. The removal of air from the chamber before the sterilization process begins also serves to generally remove air pockets from the chamber, and thereby allows steam to be more evenly distributed throughout the chamber. This allows high temperature to be uniformly established in all areas of the chamber so that all surface areas of the object will be completely sterilized.

Typical sterilizers convert ordinary tap water into steam for introduction into the sterilization chamber. A conventional heat exchanger of known design converts the tap water into steam. The steam within the chamber kills bacteria and germs and then is either drawn by suction through a vacuum mechanism or condenses back to water and runs down a drain. The steam which is drawn from the chamber by the vacuum, as well as the condensed water which runs down the drain, is typically directed to the local waste water sewage system.

The condensed water and evacuated steam which is discharged from the chamber is extremely hot. Government regulations prohibit the dumping of liquids above a certain temperature into sewer systems. Therefore, the waste water generated by conventional sterilizers must either be retained in a cooling tank or a heat exchanger, a heatsink or other cooling mechanism must be provided for removing heat from the waste water before being directed into the sewer. These retention tanks and cooling mechanisms add to the sterilizer mechanisms' purchase price and operating costs.

The tap water typically utilized by conventional sterilizers include contaminants that can be deposited on the objects being sterilized, and can also accumulate within the piping and conduits of the sterilizer mechanism. The use of tap water can therefore require an operator to further clean the objects being sterilized, as well as the sterilizer mechanism itself. Since the volumes of water utilized by conventional sterilizer mechanisms are so large, it would be generally cost prohibitive to utilize purified or distilled water to generate steam using conventional sterilizers.

Conventional sterilizers often utilize complicated, complex and expensive mechanisms such as electronic computer chips for controlling the length of the sterilization cycles, as well as the other mechanical functions of the sterilizers.

It would be desirable to provide a sterilization mechanism which prevents extremely hot waste fluids from being directed into municipal sewer systems in violation of government guidelines. It would also be desirable for such a sterilizer mechanism to be simple in construction such that it is easy to operate and relatively inexpensive to manufacture. It would also be desirable for such a mechanism to economically utilize purified water for generating steam such that contaminants are not deposited on the objects to be sterilized or the internal conduits of the sterilizer itself.

BRIEF SUMMARY OF THE INVENTION

The present invention provides an autoclave or sterilizer mechanism that converts fluid or water from a holding tank into vapor or steam for sterilizing objects placed in a chamber and then recirculates this vapor back to the holding tank at the end of the sterilization process. A first conduit extends between the holding tank and the chamber. A measuring tank receives a predetermined amount of water from the holding tank which is then converted to steam by a heat exchanger. First and second solenoid valves coupled with the first conduit control the flow of water into and out of the measuring tank. Steam created from the water in the measuring tank continues to flow through the first conduit, through a first restrictor and into the chamber. A second conduit extends between the chamber and holding tank for drawing and other fluids from the chamber and directs them back to the holding tank. A pump and ejector arrangement provides suction within the second conduit. This suction draws the fluids and steam from the chamber, through a second restrictor, through the second conduit and into the holding tank.

The present invention utilizes only a relatively small amount of water during each sterilization process, and recirculates this water back to the holding tank after each sterilization cycle. Use of distilled or purified water is therefore economically feasible with the present invention. The use of purified water generally prevents contaminants such as those found in tap water from being deposited on the objects to be sterilized and the internal conduits of the sterilizer. Extra cleaning is therefore eliminated. Since the fluids from the chamber are directed back to the holding tank, no hot fluids are discharged into the local sewer system, and no supplemental cooling mechanisms are required by the present invention.

DESCRIPTION OF THE DRAWING

The drawing shows a schematic of the water recirculating sterilizer mechanism according to the present invention.

DETAILED DESCRIPTION OF THE INVENTION

Referring now to the drawing FIGURE, there is shown a sterilizer mechanism 10 according to the present invention. A sterilization chamber 10 is provided. Objects to be sterilized, such as surgical instruments, are placed within the sterilization chamber 12.

The present invention provides a mechanism for introducing steam at relatively high temperatures into the sterilization chamber 12 for sterilizing the objects within the chamber 12 and for killing bacteria and germs which may be present on the objects. A water tank or holding tank 14 is provided, and is operatively coupled with the sterilization chamber 12 by a first conduit 16. Coupled with the first conduit 16 are a check valve 18, a first solenoid valve or first valve 20, a measuring tank 22, a second solenoid valve or second valve 24, and a heat exchanger 26. The heat exchanger 26 can be any one of a number of conventional designs, and can be adapted to transfer heat from steam in a steam line 28.

The present invention also provides a mechanism for directing or recirculating the steam, water, and other fluids from the sterilization chamber 12 back to the water tank 14. A second conduit 30 is provided which extends between the chamber 12 and the water tank 14. Suction is created in the second conduit 30 by means of an ejector 32 and pump mechanism 34 which serve to establish a venturi effect for drawing water vapor and other gasses and fluids from the sterilization chamber 12. The pump 34 draws water from the tank 14 via a feed line 36 and directs this water through an ejector 32. This ejector 32 establishes an suction force which draws fluid from the chamber 12 and through the second conduit 30.

The present invention also provides first and second restrictors 38 and 40 which restrict the flow of fluids through the respective first and second conduits 16 and 30. The first restrictor 38 serves to restrict the flow of fluids into the sterilization chamber 12 through the first conduit 16. The second restrictor 40 serves to restrict the flow of fluids out of the sterilization chamber 12. The function of the first and second restrictors 38 and 40 will be described in greater detail below.

The present invention also provides an air inlet mechanism 42 coupled with the sterilization chamber 12. The air inlet mechanism 42 includes a safety valve 44, check valve 46, third solenoid valve or third valve 48, and filter 50.

A timer or control mechanism 52 shown schematically in the drawing FIGURE is provided by the present invention and controls the operation of the first, second, third, and forth solenoid valves 20, 24, 48, and 54 during the various stages of the sterilization process according to the present invention.

Next, the operation of the present invention will be described in greater detail. Before the sterilization process begins, the operator places the objects to be sterilized within the sterilization chamber 12. At this stage, the first solenoid valve 20 is closed, the second solenoid valve 24 is open, and the third solenoid valve 48 is closed. To initiate the sterilization process, the operator engages the control mechanism or timer 52. The control mechanism 52 then opens the first solenoid valve 20 and closes the second solenoid valve 24. Opening the first solenoid valve 20 allows water from the water tank 14 to flow via the first conduit 16 into the measuring tank 22. The measuring tank 22 is adapted to hold a predetermined amount of water which will eventually be converted into steam for sterilizing the objects within the chamber 12.

When the measuring tank 22 is filled with water from the water tank 14, the control mechanism 52 can initiate operation of the pump 34 and ejector 32. The pump 34 will circulate water from the water tank 14 through the feed line 36 and through the ejector mechanism 32 which will establish a venturi effect for drawing air and fluid from the sterilization chamber 12. At this stage, the third solenoid valve 48 remains closed while the sterilization chamber 12 is being evacuated, and therefore a partial vacuum is created within the chamber 12. This initial evacuation of gasses from the sterilization chamber 12 serves to generally condition the objects within the chamber 12, and begins to remove air pockets from the chamber 12.

The control mechanism 52 will then close the first solenoid valve 20 and open the second solenoid valve 24. The control mechanism 52 will then also initiate operation of the heat exchanger 26 by opening the fourth solenoid valve 54, which allows steam to enter the heat exchange 26. During this stage, the heat exchanger 26 converts the water within the measuring tank 22 to steam. This steam then flows from the heat exchanger 26, through the first conduit 16, through the first restrictor 38, and into the sterilizer chamber 12. The high temperature steam will serve to sterilize the objects within the chamber 12 and will kill any bacteria or germs present on the objects.

After a short period of time the entire amount of water within the measuring tank 22 will have been converted to steam by the heat exchanger 26 and directed into the sterilization chamber 12. The pump 34, ejector 32, and second conduit 30 continuously draw gas, vapors, and fluids from the sterilizer chamber 12 until the chamber 12 is emptied of all fluids and steam. The second conduit 30 is not coupled with a municipal sewer, but rather is operatively coupled with the water tank 14 for directing the water vapor and other gasses and fluids from the sterilization chamber 12 back to the water tank 14. The water utilized by the present invention therefore is recirculated back to the water tank 14, and is not otherwise disposed of or discarded.

Since the water utilized by the present sterilizer mechanism 10 is continuously recirculated throughout the system over repeated sterilization processes, no waste water is directed into a municipal sewer system. Therefore, no cooling system, such as a retention tank or heatsink is required by the present invention. The cost to manufacture and operate the sterilization mechanism 10 according to the present invention is therefore relatively low.

Only a relatively small amount of water is required for creating the steam generated during each sterilization process. Virtually all of this water is recirculated to the water tank 14 via the second conduit 30. Therefore, the sterilizer 10 according to the present invention requires only a relatively small quantity of water over the course of repeated cycles of sterilization. The use of purified or distilled water during the sterilization process according to the present invention is therefore cost effective. Since purified water does not contain the contaminants found in tap water, such contaminants are not deposited on the objects being sterilized or the interior conduits of the sterilizer itself. Extra cleaning steps are therefore eliminated by the sterilizer 10 according to the present invention.

The first and second restrictors 38 and 40 are provided for generally controlling the flow of steam and fluids into and out of the sterilization chamber 12. The first restrictor 38 can be generally less restricted than the second restrictor 40. The restrictors 38 and 40 allow steam to accumulate within the chamber 12 and prevent the pump 34 and ejector 32 from drawing the steam out of the chamber 12 before the steam has a chance to sterilize the objects within the chamber 12. Once the predetermined amount of water within the measuring tank 22 has been converted to steam which fills the chamber 12, the pump 34 and ejector 32 continue to draw fluid and steam from the chamber 12 until the chamber 12 is relatively dry.

The check valve 18 prevents high pressure steam from backing up into the water tank 14. Safety valve 44 would allow high pressure steam to be discharged from the chamber 12 before the pressure within the chamber 12 exceeds a level that might damage the chamber 12. The third solenoid valve 48 is opened after the sterilization process is completed and serves to break the vacuum within the chamber 12, thereby allowing the operator to easily open the chamber door. A filter 50 insures that only relatively clean air is introduced into the chamber 12 through the third solenoid valve 48. The check valve 46 prevents steam or other fluids from being discharged from the chamber 12 through the third solenoid valve 48 and filter 50, and thereby prevents the filter from being damaged.

Having described the preferred embodiment, other features of the present invention will undoubtedly occur to those versed in the art, as will numerous modifications and alterations in the embodiments of the invention illustrated, all of which may be achieved without departing from the spirit and scope of the invention as defined in the appended claims.

What is claimed is:

1. A sterilization apparatus, comprising:
   a) a sterilization chamber within which objects to be sterilized are placed;
   b) a tank within which water is held;
   c) a first conduit extending between the tank and the sterilization chamber;
   d) a heat source operatively coupled with the first conduit for converting the water within the first conduit to steam, said steam being directed into the sterilization chamber by the first conduit to sterilize the objects within the sterilization chamber;
   e) a measuring means for measuring a predetermined amount of water from the tank, said measuring means being operatively coupled with the first conduit for directing said predetermined amount of water from the measuring means into the first conduit, said predetermined amount of water being sufficient once converted to steam and directed into the sterilization chamber to completely sterilize objects placed in the sterilization chamber;
   f) a control means operatively coupled with the first conduit for causing the first conduit to direct steam into the sterilization chamber not more than a single time during the process of sterilizing the objects placed in the sterilization chamber;
   g) a second conduit operatively coupled between the sterilization chamber and the tank, said second conduit operatively directs water from the sterilization chamber back to the tank;
   h) said measuring means further comprises a measuring tank which receives a predetermined amount of water from the tank which is converted into a predetermined amount of steam by the heat source and is directed to the sterilization chamber by the first conduit;
   i) a first valve operatively positioned between the water tank and the measuring tank, and a second valve operatively positioned between the measuring tank and the sterilization chamber, said first valve being opened and the second valve being closed by the control means, before a particular sterilization process has begun such that the measuring tank is allowed to fill with a predetermined amount of water, and said first valve is closed and the second valve is open by the control means throughout the entire sterilization process such that the water in the measuring tank is converted to a predetermined amount of steam which is directed into the sterilization chamber.

2. The apparatus in accordance with claim 1, and further comprising:
   a) a first restrictor means for restricting the flow of steam into the sterilization chamber from the first conduit;
   b) a second restrictor means for restricting the flow of fluids out of the sterilizations chamber into the second conduit; and
   c) wherein the first restrictor means is less restricted than the second restrictor means such that when the sterilization process is underway the sterilization chamber is filled with steam which is then removed from the chamber through the second restrictor means and second conduit.

* * * * *